US00PP32563P2

(12) United States Plant Patent
O'Connell

(10) Patent No.: US PP32,563 P2
(45) Date of Patent: Dec. 1, 2020

(54) ***AEONIUM* PLANT NAMED 'SUN DANCER'**

(50) Latin Name: ***Aeonium* hybrid**
Varietal Denomination: Sun Dancer

(71) Applicant: Altman Specialty Plants, Inc, Vista, CA (US)

(72) Inventor: Renee O'Connell, Escondido, CA (US)

(73) Assignee: Altman Specialty Plants, Inc, Vista, CA (US)

( * ) Notice: Subject to any disclaimer, the term of this patent is extended or adjusted under 35 U.S.C. 154(b) by 0 days.

(21) Appl. No.: 16/873,314

(22) Filed: Mar. 17, 2020

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct cultivar of *Aeonium* plant named 'Sun Dancer' is disclosed, characterized by very even, concentric rosettes, comprised of an abundance of green leaves, colored marginally with creamy white, and arranged in an attractive, variegated geometric pattern. Further, the new cultivar 'Sun Dancer' freely offsets, enabling increased and faster propagation of the cultivar. In addition, the robust growth, in combination with the freely offsetting characteristic of the new cultivar 'Sun Dancer', results in the clusters at an early age, and therefore enhances production intervals. The new variety is an *Aeonium*, part of the Crassulaceae complex that includes *Aeonium, Echeveria, Graptopetalum, Sedum* and others. *Aeonium* is a popular genus, typically produced as container plants for the patio or as landscape plants.

2 Drawing Sheets

Figure 1:
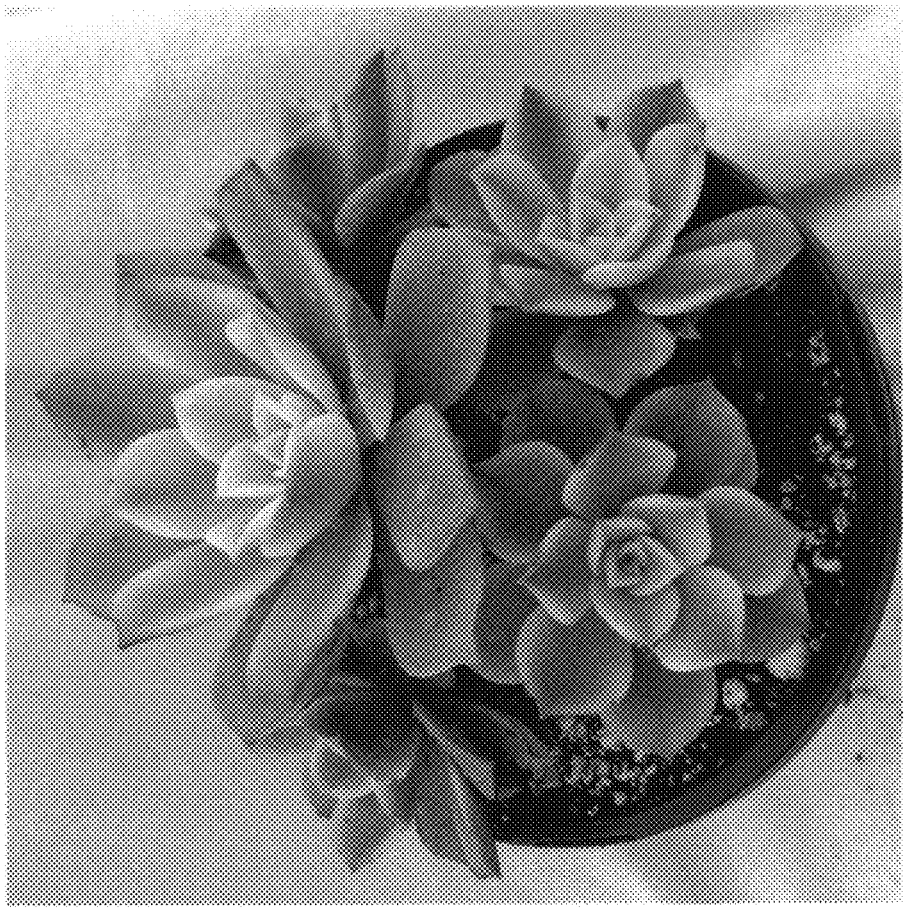

Latin name of the genus and species: *Aeonium* hybrid.
Variety denomination: 'SUN DANCER'.

BACKGROUND OF THE INVENTION

The new cultivar, *Aeonium* 'Sun Dancer', was found by the inventor, Renee O'Connell, as the result of a crossing made February 2015 as part of a planned breeding program. The seed parent variety is the unpatented proprietary variety referred to as *Aeonium* 'K06'. The pollen parent is the unpatented proprietary variety *Aeonium* 'KI 10'. *Aeonium* 'Sun Dancer' was selected by the inventor, Renee O Connell, in March 2016 from a group of seedlings resulting from the 2015 crossing, at a commercial greenhouse in Vista, Calif.

Asexual reproduction of the new cultivar 'Sun Dancer' was first performed in Vista, Calif., at a commercial greenhouse, by vegetative cuttings in April 2016. 'Sun Dancer' has since produced multiple generations and has shown that the unique features of this cultivar are stable and reproduced true to type.

SUMMARY OF THE INVENTION

The cultivar 'SUN DANCER' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUN DANCER' These characteristics in combination distinguish 'SUN DANCER' as a new and distinct *Aeonium* cultivar:

1. *Aeonium* 'Sun Dancer' exhibits a rapid and robust growth rate, enhancing production rates in a commercial nursery.
2. *Aeonium* 'Sun Dancer' offsets prolifically, and in combination with its fast and robust growth rate, enhances propagation production in a commercial nursery.
3. *Aeonium* 'Sun Dancer' displays multicolored rosettes of lemon yellow and green, margined with red during certain conditions.
4. *Aeonium* 'Sun Dancer', unlike most *Aeoniums* that are largely dormant during the hot months, demonstrated rooting and growth during July and August, allowing for propagation all year round, whereas most *Aeoniums* must be treated as seasonal plants in hot climates.
5. *Aeonium* 'Sun Dancer', exhibiting lemon yellow variegation, and robust growth, is an excellent choice for ready-to-use patio gardens, in the landscape and for other decorative uses.

PARENTAL COMPARISON

Plants of the new cultivar 'SUN DANCER' are similar to plants of the seed parent in most horticultural characteristics, however, plants of the new cultivar 'SUN DANCER' differ in the following;

1. *Aeonium* 'Sun Dancer' produces more offsets than *Aeonium* 'K06'.
2. *Aeonium* 'Sun Dancer' exhibits variegation of the rosettes, not exhibited by *Aeonium* 'K06'.
3. *Aeonium* 'Sun Dancer' exhibits more resistance to the dormancy initiated by hot weather than does *Aeonium* 'K06'.
4. *Aeonium* 'Sun Dancer' grows faster than does *Aeonium* 'K06'.

Plants of the new cultivar 'SUN DANCER' are similar to plants of the pollen parent in most horticultural characteristics, however, plants of the new cultivar 'SUN DANCER' differ in the following;

1. *Aeonium* 'Sun Dancer' exhibits larger rosettes than *Aeonium* 'KI 10'.
2. *Aeonium* 'Sun Dancer' grows at a faster rate than *Aeonium* 'KI 10'.
3. *Aeonium* 'Sun Dancer' exhibits more resistance to the dormancy initiated by hot weather than does *Aeonium* 'KI 10'.
4. *Aeonium* 'Sun Dancer' produces a larger plant than does *Aeonium* 'KI 10', making it more suitable for the landscape and in large containers for patio use.

COMMERCIAL COMPARISON

Plants of the new cultivar 'SUN DANCER' are comparable to the unpatented, commercial variety *Aeonium* 'Kiwi'. The two *Aeonium* varieties are similar in most horticultural characteristics; however, the new variety 'SUN DANCER' differs in the following:

1. *Aeonium* 'Kiwi' produces smaller rosettes than does *Aeonium* 'Sun Dancer'.
2. *Aeonium* 'Kiwi' is not as fast growing as *Aeonium* 'Sun Dancer'.
3. *Aeonium* 'Kiwi' does not produce as large a plant as *Aeonium* 'Sun Dancer'.

Plants of the new cultivar 'SUN DANCER' can also be comparable to the unpatented commercial variety *Aeonium* 'Zwartkop'. The two *Aeonium* varieties are similar in most horticultural characteristics; however, the new variety 'SUN DANCER' differs in the following:

1. *Aeonium* 'Sun Dancer' shows a resistance to the summer dormancy and can be rooted in full sun during hot months, whereas *Aeonium* 'Zwartkop' shuts down during this summer period, closing its rosettes to conserve water.
2. *Aeonium* 'Sun Dancer' produces variegated rosettes of lemon yellow and green, whereas *Aeonium* 'Zwartkop' produces dark rosettes.
3. *Aeonium* 'Sun Dancer' offsets at an early age, whereas *Aeonium* 'Zwartkop' does not offset until it is larger.
4. *Aeonium* 'Sun Dancer' produces a more compact cluster than does *Aeonium* 'Zwartkop'.

BRIEF DESCRIPTION OF THE PHOTOGRAPHS

The accompanying photograph in FIG. 1 illustrates in full color a typical of plant of *Aeonium* 'Sun Dancer' grown in a shade house in Vista, Calif. at a light intensity of approximately 3500 fc.

Figure 2:
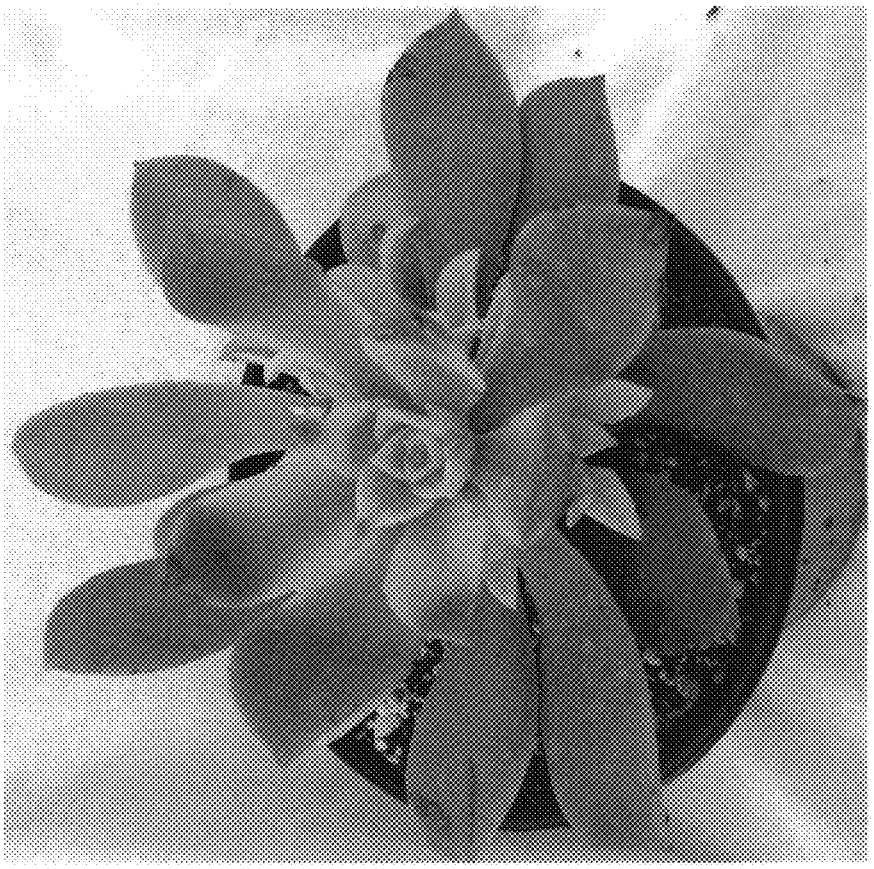

FIG. 2 illustrates a different plant of similar age growing outdoors in full sun (approximately 9000 foot candles) in Vista, Calif. Age of the plants photographed is approximately 5 months from a rooted cutting.

The photographs were taken using conventional techniques and although colors may appear different from actual colors due to light reflectance it is as accurate as possible by conventional photographic techniques. All photographs provided by the breeder.

DETAILED BOTANICAL DESCRIPTION

In the following description, color references are made to The Royal Horticultural Society Colour Chart, 2007, except where general terms of ordinary dictionary significance are used. The following observations and measurements describe 'Sun Dancer' plants in a commercial shade house in Vista, Calif. Temperatures ranged from approximately −1° C. to 29° C. night and day. No artificial light, photoperiodic treatments or chemical treatments were given to the plants. Natural light conditions were approximately 3500 fc of light. Measurements and numerical values represent averages of typical plant types.

Botanical classification: *Aeonium* hybrid 'SUN DANCER'.

PROPAGATION

Type of propagation typically used: Terminal vegetative divisions.

Time to initiate roots: About 18 days at approximately 24° C.

Root description: Fibrous, brown, not accurately measured with a color chart.

PLANT

Age of plant described: Approximately 4 months.

Container size of the plant described: 6 inch.

Growth habit: Upright, caulescent, with a terminal rosette, freely offsetting from below rosette and between leaves of the rosette to produce cluster.

Height: Approximately 14 cm to top of highest leaf Height in cm to top of inflorescence is unknown as plant has been undergoing propagation, and has not yet flowered.

Plant spread: 20 cm.

Growth rate: Moderately fast.

Branching characteristics: Freely offsetting.

Rosettes per plant: Average range 7 to 10.

FOLIAGE

Leaf:

*Arrangement*.—Rosulate.

*Average length*.—Outer rosette leaf approximately 10 cm. Inner rosette leaf approx. 2 to 4 cm.

*Average width*.—Outer rosette leaf approximately 3.2 cm. Inner rosette leaf approx. 1.2 cm.

*Width at base*.—1.0 cm.

*Shape of blade*.—Spatulate.

*Apex*.—Mucronate.

*Base*.—Cuneate.

*Margin*.—Entire. Towards apex fine, irregular sparse dentation.

*Texture of top surface*.—Glabrous.

*Texture of bottom surface*.—Glabrous.

*Quantity of leaves per rosette*.—Average range 15 to 20.

*Color*.—Young foliage upper side: Near RHS Yellow 2D, center and base flushed near Green 137D. Young foliage, under side: Near RHS Yellow 2D, center and base flushed near Green 137D. Apex and margin irregularly blotched Red 45D. Mature foliage upper side: Near RHS Green 138A. Base Yellow-Green 144D. Apical margin has a thin flush near Red 46D. Mature foliage, under side: Near RHS Green 138A.

Base Yellow-Green 144D. Apical margin has a thin flush near Red 46D.

*Venation*.—There is no visual appearance of venation.

FLOWER

Flowering not observed to date.

REPRODUCTIVE ORGANS

Flowering not observed to date.

OTHER CHARACTERISTICS

Fruits and seeds: Plant has not flowered or produced fruits and seeds to date.

Temperature tolerance: Tolerates temperatures from approximately −2 to 32° C.

Disease/pest resistance: Displays the same disease and pest resistance of any other comparable *Aeonium*.

Drought tolerance: Tolerates at least 3 weeks of high temperatures without supplemental water, showing no serious damage to plant.

What is claimed is:

1. A new and distinct cultivar of *Aeonium* plant named 'SUN DANCER' as herein illustrated and described.

* * * * *